(12) United States Patent
Bar-Tal et al.

(10) Patent No.: US 8,900,225 B2
(45) Date of Patent: Dec. 2, 2014

(54) AUTOMATIC ABLATION TRACKING

(75) Inventors: Meir Bar-Tal, Haifa (IL); Aharon Turgeman, Zichron Ya'acov (IL); Noam Seker Gafni, Kiryat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 388 days.

(21) Appl. No.: 13/465,103

(22) Filed: May 7, 2012

(65) Prior Publication Data
US 2013/0296845 A1  Nov. 7, 2013

(51) Int. Cl.
*A61B 18/04* (2006.01)

(52) U.S. Cl.
USPC .......................................................... 606/34

(58) Field of Classification Search
USPC .......................................................... 606/34
See application file for complete search history.

(56) References Cited

U.S. PATENT DOCUMENTS

| | | | |
|---|---|---|---|
| 7,438,714 B2* | 10/2008 | Phan | 606/49 |
| 2011/0054304 A1 | 3/2011 | Markowitz et al. | |
| 2011/0125150 A1 | 5/2011 | Deno et al. | |
| 2011/0130648 A1 | 6/2011 | Beeckler et al. | |

FOREIGN PATENT DOCUMENTS

| | | | |
|---|---|---|---|
| EP | 2 085 026 A1 | | 8/2009 |
| WO | WO 2009/100098 A2 | | 8/2009 |

OTHER PUBLICATIONS

U.S. Appl. No. 13/017,469, filed Jan. 31, 2011.

* cited by examiner

*Primary Examiner* — George Manuel
(74) *Attorney, Agent, or Firm* — Wayne C. Jaeschke, Jr.

(57) ABSTRACT

A method for performing a medical procedure includes bringing a probe into contact with an organ in a body of a patient. A map of the organ is displayed, and the location of the probe relative to the map is tracked. A therapy is applied via the probe at multiple tissue sites in the organ with which the probe is brought into contact. Stability of the contact between the probe and the tissue sites is assessed while applying the therapy. The map is automatically marked, responsively to the assessed stability, to indicate the tissue sites at which the therapy was applied.

27 Claims, 5 Drawing Sheets

AUTOMATIC ABLATION TRACKING

FIELD OF THE INVENTION

The present invention relates generally to systems and methods for invasive medical treatment, and specifically to tracking and visualizing such treatment.

BACKGROUND OF THE INVENTION

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intracardiac ablation therapy are commercially available, such as the CARTO™ system offered by Biosense Webster Inc. (Diamond Bar, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus to keep track of the progress of the procedure.

U.S. Patent Application Publication 2011/0125150, whose disclosure is incorporated herein by reference, describes a system and method for assessing effective delivery of ablation therapy to a tissue in a body. A 3D anatomical map of the tissue is generated and displayed. An index is generated corresponding to a location and indicating a state of ablation therapy at the location. The index may be derived from factors such as the duration an ablation electrode is present at the location, the amount of energy provided, the degree of electrical coupling between the electrode and the tissue, and temperature. A visual characteristic (e.g., color intensity) of a portion of the anatomical map corresponding to the location is altered responsively to the index.

SUMMARY OF THE INVENTION

Embodiments of the present invention that are described hereinbelow provide methods and systems for enhanced visualization of invasive therapies.

There is therefore provided, in accordance with an embodiment of the present invention, a method for performing a medical procedure. The method includes bringing a probe into contact with an organ in a body of a patient, displaying a map of the organ and tracking a location of the probe relative to the map. A therapy is applied via the probe at multiple tissue sites in the organ with which the probe is brought into contact. A stability of the contact between the probe and the tissue sites is assessed while applying the therapy, and the map is automatically marked, responsively to the assessed stability, to indicate the tissue sites at which the therapy was applied.

In some embodiments, automatically marking the map includes accepting a definition of a stability criterion, and marking the sites at which the assessed stability satisfied the stability criterion. Different, respective definitions may be set for different regions of the organ. In a disclosed embodiment, the organ has a wall that contains the tissue sites to which the therapy is applied, and setting the different, respective definitions includes setting different thresholds responsively to variations of a thickness of the wall among the different regions. Additionally or alternatively, the stability criterion specifies a minimum time, and the map is automatically marked to indicate the tissue sites at which the probe was stable for no less than the minimum time.

In a disclosed embodiment, assessing the stability includes measuring changes in the location of the probe during application of the therapy, while compensating for a movement of the body, such as compensating for variations in a position of the heart due to respiration. Additionally or alternatively, assessing the stability includes measuring a force of the contact between the probe and the tissue sites.

In some embodiments, applying the therapy includes ablating the tissue sites. Automatically marking the map may include measuring an electrical impedance at the tissue sites using the probe, and marking the tissue sites responsively to a change in the impedance during the therapy. Additionally or alternatively, automatically marking the map includes measuring electrophysiological signals at the tissue sites using the probe, and marking the tissue sites responsively to a change in the electrophysiological signals during the therapy. Further additionally or alternatively, automatically marking the map includes measuring a temperature at the tissue sites using the probe, and marking the tissue sites responsively to a change in the temperature during the therapy. As yet another example, automatically marking the map includes measuring electrical power delivered to the tissue sites by the probe, and marking the tissue sites responsively to a cumulative power applied to each of the tissue sites during the therapy.

There is also provided, in accordance with an embodiment of the present invention, apparatus for performing a medical procedure, which includes an invasive probe, which is configured to be brought into contact with an organ in a body of a patient and to apply a therapy at multiple tissue sites in the organ with which the probe is brought into contact. A processor is coupled to the probe and is configured to display a map of the organ and to track a location of the probe relative to the map, to assess a stability of the contact between the probe and the tissue sites while applying the therapy, and to automatically mark the map, responsively to the assessed stability, to indicate the tissue sites at which the therapy was applied.

There is additionally provided, in accordance with an embodiment of the present invention, a computer software product, including a computer-readable medium in which program instructions are stored, which instructions are configured to be read by a processor that is coupled to an invasive probe for applying a therapy at multiple tissue sites in an organ with which the probe is brought into contact, and cause the processor to display a map of the organ and to track a location of the probe relative to the map, to assess a stability of the contact between the probe and the tissue sites while applying the therapy, and to automatically mark the map, responsively to the assessed stability, to indicate the tissue sites at which the therapy was applied.

The present invention will be more fully understood from the following detailed description of the embodiments thereof, taken together with the drawings in which:

DETAILED DESCRIPTION OF EMBODIMENTS

Overview

Figure 1:
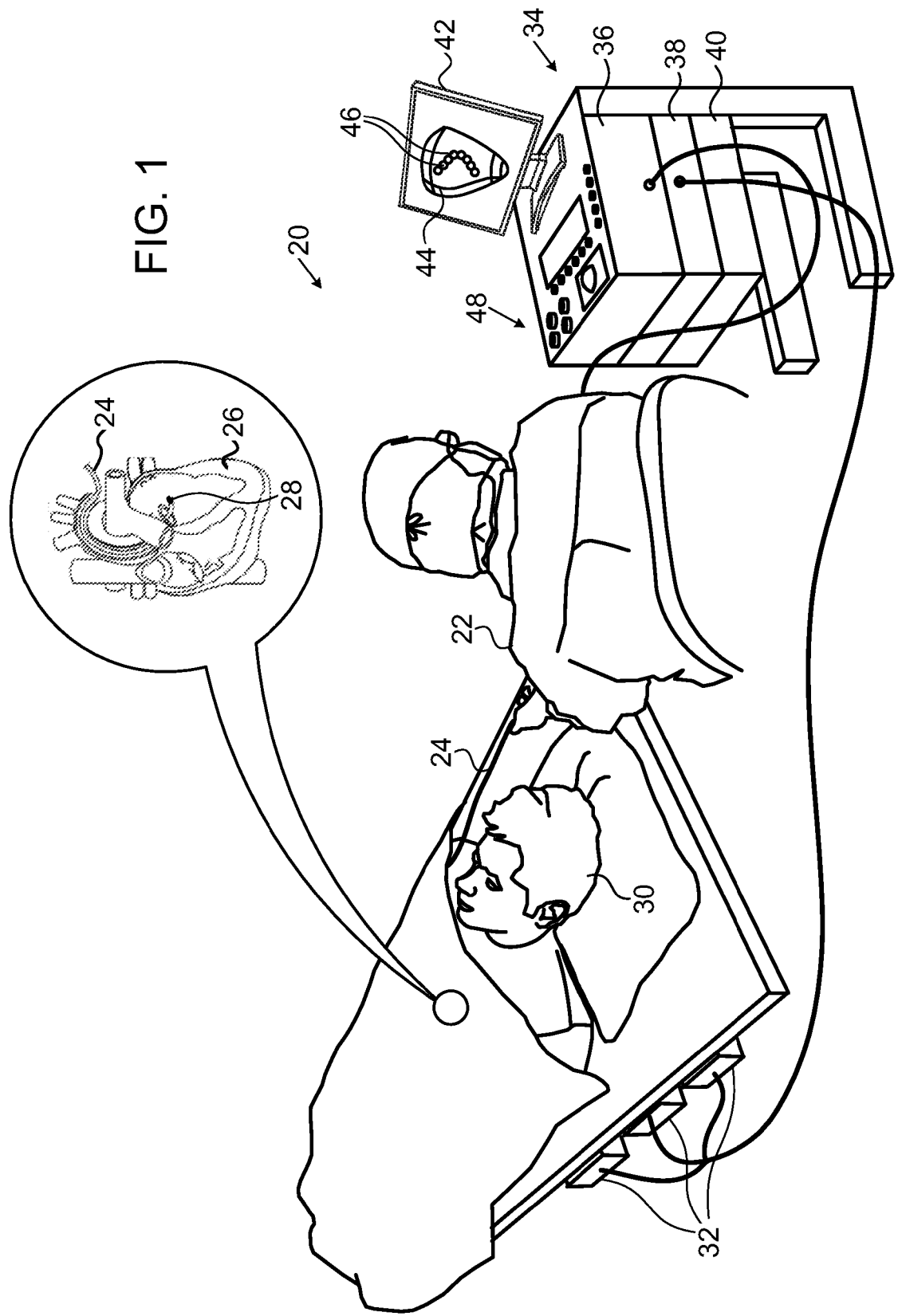
FIG. 1 is a schematic pictorial illustration of a system for intracardiac ablation, in accordance with an embodiment of the invention.

In catheter-based treatment systems that are known in the art, such as the above-mentioned CARTO system, a physician conducting an ablation procedure marks ablation locations on a map of the organ by manually operating the controls of the system. The physician typically marks a given treatment location once she/he considers that the location has been adequately treated, based on experience and parameter readings that are available during the procedure. The parameters may include, for example, electrophysiological signals (also referred to as ECG), the location of the region being ablated, the elapsed time of ablation at a given site, the ablation power applied, the force (magnitude and direction) registered by the catheter, and one or more temperature measurements. Depending on the catheter being used in the procedure, other parameters may also be relevant, such as a rate of irrigation of the distal end of the catheter and impedances registered by electrodes at the distal end of the catheter.

In embodiments of the present invention, a processor coupled to the catheter receives the parameters described above. On the basis of preset ablation criteria (at least some of which may be set by the physician or other system operator), the processor marks the map automatically, instead of requiring the operator to mark the map manually, and keeps track of ablation parameters recorded at each site. Since the marking is computerized, it is not subject to inaccuracies caused by human map marking. The automated record-keeping enables the operator to review sites that have already been treated, and if necessary to choose further sites to ablate.

The map upon which the ablations are marked may be divided into non-overlapping zones, such as in a Voronoi diagram. The ablation criteria may be preset according to zone characteristics, such as the zone position within the heart, a mean thickness of the zone heart wall, a local impedance of the wall, and/or a contractility of the wall.

Although the embodiments described below relate specifically to performance of intracardiac ablation, using a catheter of suitable design, the principles of the present invention may similarly be applied in tracking and visualizing not only ablation but also other sorts of treatments, which may be applied to the heart or to other organs, using either catheters or other suitable types of invasive probes.

In the embodiments that are disclosed below, an operator of a cardiac ablation system brings the distal end of a catheter into contact with the inner heart wall in a body of a patient. The ablation system displays a map of the heart and tracks and displays the location of the catheter in the heart relative to the map. The operator manipulates the catheter and controls the system to apply ablation therapy at multiple tissue sites in the heart with which the catheter is brought into contact. Based on the catheter location measurements, the system assesses the stability of contact between the catheter and the tissue sites while applying the therapy. On the basis of the assessed stability, the system then automatically marks the map to indicate the tissue sites at which the therapy was applied.

Typically, the system marks sites on the map that satisfy a certain stability criterion, which may be defined by the system operator. The stability criterion may require, for example, that the catheter dwell at a given site (to within a certain maximum location deviation) for at least a certain minimum ablation time, and possibly that the force between the catheter and the heart wall during this period be no less than a predefined minimum force. Sites satisfying the criterion are marked on the map, while those that do not satisfy the criterion are not marked, or are marked in a way that distinguishes them from "stable" ablation sites. As noted earlier, the definition of the stability criterion may vary for different regions of the heart, depending on variations in the thickness of the heart wall, among other factors. In assessing the stability of the catheter during the ablation, the system may compensate for movement of the body, and specifically may compensate for variations in the position of the heart due to respiration of the patient.

Additionally or alternatively, the system may apply other criterion in automatically tracking the ablation process and in marking the corresponding sites on the map of the heart. For example, the system may measure the electrical impedance at the ablated tissue sites using the catheter, and mark the tissue sites depending on the change in the impedance during the therapy. As other examples, the system may mark the tissue sites responsively to changes in electrophysiological signals (such as ECG) measured by the catheter and/or to changes in temperature measured by the catheter during the therapy. Another factor that the system may use in determining how to mark the ablation sites is the cumulative electrical power delivered to the tissue sites by the catheter.

Typically, the system allows the operator to select the parameters that are to be used in marking ablation sites and in setting thresholds to distinguish between sites that have been adequately ablated and those that may not have been adequately ablated. The operator may choose any suitable combination of the measured parameters for this purpose. Depending on the selected parameters and the applicable thresholds, the system may decide which sites to mark or not mark, and/or may vary the appearance of the marks that it places on the map.

System Description

FIG. 1 is a schematic, pictorial illustration of a cardiac mapping and ablation system 20, which operates in accordance with an embodiment of the invention. System 20 may be based, for example, on the above-mentioned CARTO system, with suitable additions to the system software. System 20 comprises a probe, such as a catheter 24, and a control console 34. In the embodiment described hereinbelow, catheter 24 is used in ablating sites of arrhythmias in one or more chambers of a heart 26 of a patient 30. Alternatively, catheter 24 or other suitable probes may be used, mutatis mutandis, for other therapeutic purposes in the heart or in other body organs.

An operator 22, such as a cardiologist, inserts catheter 24 through the vascular system of patient 30 so that the distal end of the catheter enters a chamber of heart 26. Operator 22 advances the catheter so that an electrode 28 at the distal tip of the catheter engages endocardial tissue at desired ablation sites. Catheter 24 is typically connected by a suitable connector at its proximal end to console 34, and specifically to a radio frequency (RF) generator 36, which generates RF energy for transmission via catheter 24 to electrode 28. Operator 22 actuates RF generator 36 to ablate tissue at suspected sites of arrhythmia in the heart.

In this pictured embodiment, system 20 uses magnetic position sensing to determine position coordinates of the distal end of catheter 24 inside heart 26. For this purpose, a driver circuit 38 in console 34 drives field generators 32 to generate magnetic fields within the body of patient 30. Typically, field generators 32 comprise coils, which are placed below the patient's torso at fixed, known positions. These coils generate magnetic fields in a predefined working volume that contains heart 26. A magnetic field sensor (not shown) within the distal end of catheter 24 generates electrical signals in response to these magnetic fields. A signal processor 40 processes these signals in order to determine the position coordinates of the distal end of catheter 24, typically including both location and orientation coordinates. This method of position sensing is implemented in the above-mentioned CARTO system and is well known in the art. Alternatively or additionally, system 20 may use other methods of position sensing that are known in the art, such as ultrasonic or electrical impedance-based methods.

In addition, catheter 24 may comprise a force sensor (not shown) in its distal end, for measuring the contact force between the catheter tip and the wall of heart 26. The Smart-Touch™ catheter developed by Biosense Webster Inc. for the CARTO system offers this sort of capability. A catheter of this sort is described, for example, in U.S. Patent Application Publication 2011/0130648, whose disclosure is incorporated herein by reference. The force measurement is useful in ensuring that electrode 28 is in sufficiently firm contact with the heart wall to effectively transfer RF energy and ablate the heart tissue.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26. The map may indicate cardiac electrophysiological activity measured by catheter 24, as well as providing visual feedback regarding the position of the catheter in the patient's body and status information and guidance regarding the procedure that is in progress. Other parameters that may be measured by catheter 24 and by other elements of system 20 and shown on display 42 may include, for example, contact force between the catheter and heart tissue, electrical impedance of the heart tissue, local temperature, and RF power delivered through the catheter.

Processor 40 assesses the parameters that it receives from system 20 as indicators of the adequacy of ablation at each treated site in heart 26. When the ablation parameters at a given site meet certain predefined criteria, the processor automatically places a mark 46 on map 44 to indicate the site. The processor may vary the appearance of marks 46 (such as their color) in response to the parameters at each site. The criteria for automatic marking of the ablation sites may be preconfigured, or they may, alternatively or additionally, be set by operator 22, typically using user interface controls 48 and on-screen menus.

Although in the illustrated embodiment, catheter 24 is manipulated manually by operator 22, system 20 may alternatively or additionally comprise an automated mechanism (not shown) for maneuvering and operating the catheter within the body of patient 30. In such embodiments, processor 40 generates a control input for controlling the motion of catheter 24 based on the signals provided by the magnetic field sensor in the catheter and other system parameters, such as those mentioned above.

Figure 2:
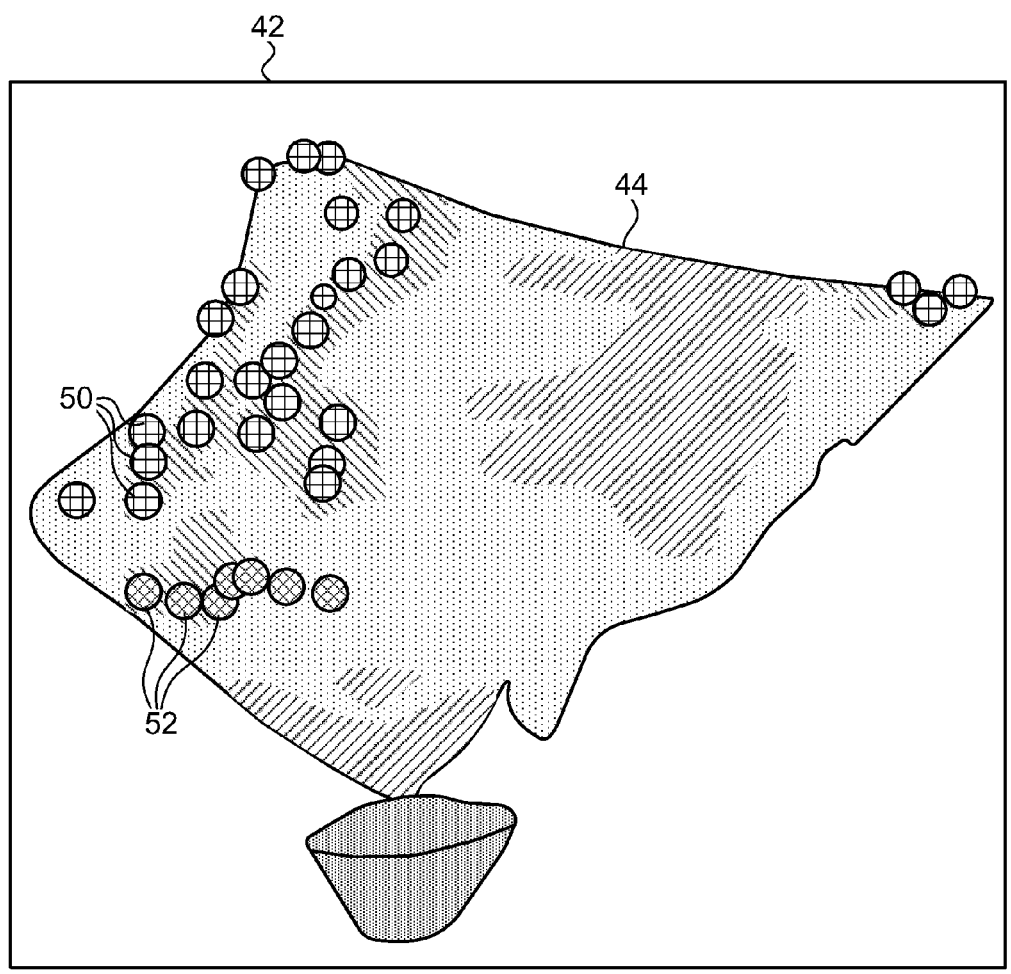
FIG. 2 is a schematic representation of a 3D map of a heart chamber that is presented on a display screen, in accordance with an embodiment of the invention.

FIG. 2 is a schematic representation of map 44 as it appears on display 42, in accordance with an embodiment of the present invention. Map 44 is a 3D representation of a chamber of the heart, which is colored to show local electrical activity, as in the above-mentioned CARTO system. (Colors are represented by hatching in the figure.) The map may be generated based simply on position measurements made using catheter 24, or alternatively, these position measurements may be registered with a pre-acquired image of the heart (such as a CT, MRI, or ultrasound image) in order to create the map.

Processor 40 has placed marks 50, 52 on map 44 to indicate sites that have been ablated by catheter 24. Typically, the processor automatically marks sites at which the ablation parameters, such as dwell time and force applied by the catheter against the tissue, meet the predefined criteria. Marks 50 and 52 may be colored differently to indicate different ranges of measured parameters. Normally, as noted above, the criteria to be applied by processor 40 in marking ablation sites may be defined by operator 22. Additionally or alternatively, the operator may choose to mark sites manually by manipulating appropriate system controls.

Although FIGS. 1 and 2 show a particular system configuration and application environment, the principles of the present invention may similarly be applied in other mapping and therapeutic applications using not only catheters, but also probes of other types, both in the heart and in other body organs and regions.

Methods for Automatic Marking

Figure 3:
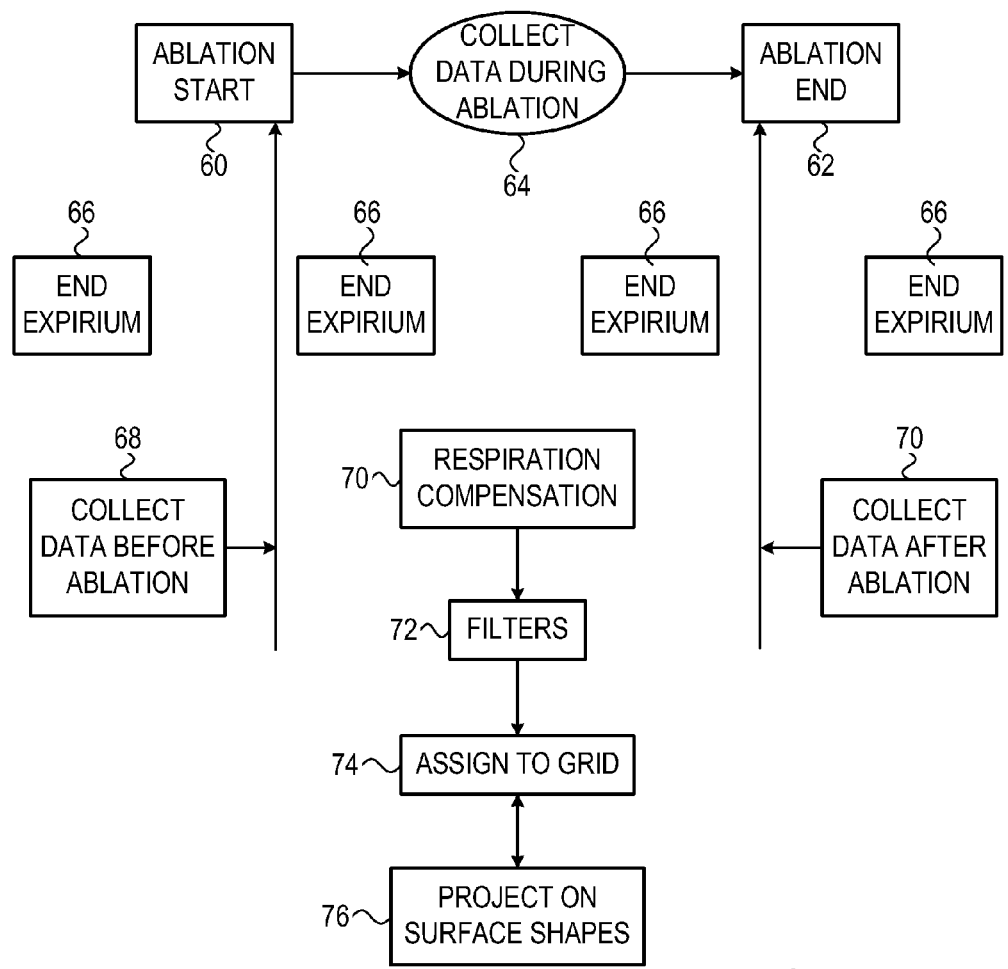
FIG. 3 is a flow chart that schematically illustrates a method for tracking intracardiac ablation, in accordance with an embodiment of the invention.

FIG. 3 is a flow chart that schematically illustrates a method for tracking intracardiac ablation, in accordance with an embodiment of the invention. The method is described, for the sake of clarity and convenience, with reference to system 20. As noted above, however, the principles of the methods described hereinbelow may similarly be applied in other systems and application environments.

Processor 40 collects data continuously during the operation of system 20 and saves the data in a cyclic buffer in memory. The data are flushed from the buffer on a first-in/first-out basis. Data processing is initiated when ablation starts, at an initiation step 60, typically when operator 22 activates RF generator 36. At this point, processor 40 is able to collect and process data that accumulated in the buffer before ablation, at a pre-ablation collection step 68. The processor continues collecting data during ablation, at a peri-ablation collection step 64, until the RF generator is deactivated, at an ablation termination step 62. The processor may continue collecting data after step 62, at a post-ablation collection step 70, for use in assessing the results of the ablation at the current site.

Performing ablation at any given site typically takes at least several seconds, and may take as long as a minute. During this period, patient 30 will typically take one or more breaths, with the result that the location of heart 26 shifts (along with other parts of the patient's chest) relative to field generators 32. These breaths are indicated in FIG. 3 by end-expirium points 66. As a result of this respiratory motion of the chest, position readings made by processor 40 with respect to catheter 24 will shift cyclically in synchronization with the respiration cycle, and the catheter coordinates will change even when the catheter is stably held in contact with a given ablation site.

In order to eliminate this confusing effect of respiratory motion on the catheter position, processor 40 corrects the position coordinates to compensate for respiration, at a respiration compensation step 70. Typically, processor 40 uses end-expirium points 66 as a baseline, determines the shift of heart 26 relative to this baseline at each point during the respiratory cycle, and then subtracts out this shift from the catheter coordinates in order to project all position readings to the equivalent end-expirium location. When the catheter is actually moving relative to the heart, step 70 will convert the sequence of catheter position reads to a linear path between the start- and end-points of the movement. A method of compensation for respiratory motion that may be used at this step is described, for example, in U.S. patent application Ser. No. 13/017,469, whose disclosure is incorporated herein by reference.

Figure 5:
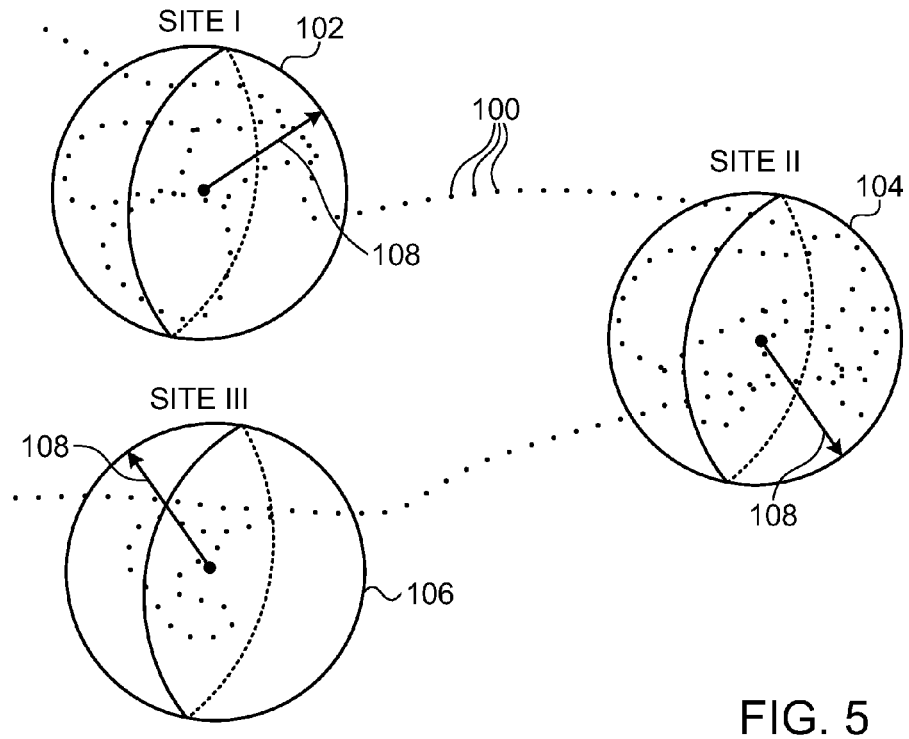
FIG. 5 is a schematic representation of a map of a chamber of the heart showing a series of catheter location data, in accordance with an embodiment of the invention.
Figure 6:
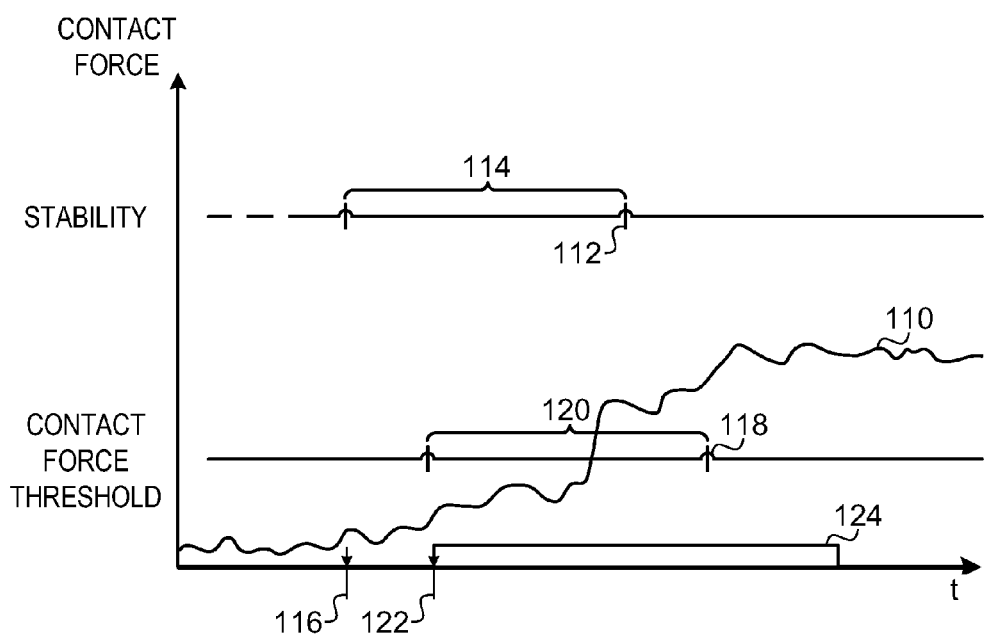
FIG. 6 is a schematic plot of catheter contact force at an ablation location, in accordance with an embodiment of the invention.
Figures 7, 8:
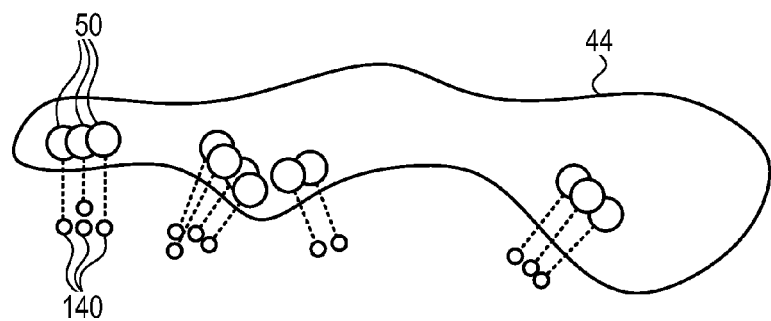
FIG. 7 is a schematic representation of a window on an ablation mapping display screen, in accordance with an embodiment of the invention.
FIG. 8 is a schematic representation of a 3D map of a heart chamber showing ablation marks applied to the map.

Processor 40 filters the collected data to identify ablation sites that should be marked on map 44, at a filtering step 72. At this step, the processor evaluates whether a given site meets predefined criteria in terms of stability of the contact between the probe and the tissue and other factors, so as to qualify to be marked. This step is described in greater detail below with reference to FIG. 4. Sites that satisfy the filter criteria are selected to be marked on the map, while sites that do not satisfy the criteria are discarded. FIGS. 5 and 6 show how stability criteria are applied in this step, while FIG. 7 shows a user interface window that can be used by operator 22 (or other personnel) to set the filter criteria.

When a site satisfies the filter criteria, processor 40 assigns the site data to a specific position in the 3D space corresponding to map 44, at a grid assignment step 74. In other words, even if there is some residual variation in measured catheter coordinates, following respiration compensation, during the ablation, the processor chooses a particular coordinate location to be marked, such as the center of mass of the compensated coordinate values. The position may be a specific voxel in a 3D grid, for example, or it may correspond to a zone of the map, such as zones in a Voronoi diagram corresponding to the map shape.

Processor 40 then projects the volume points assigned at step 74 to corresponding locations on the surface of map 44, and creates marks 50, 52 at these surface locations, at a projection step 76. This step is described in greater detail with reference to FIG. 8 below.

Figure 4:
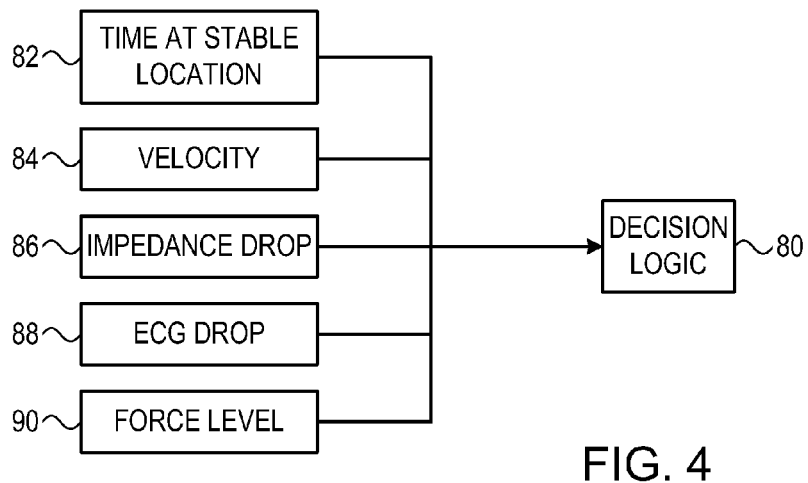
FIG. 4 is a flow chart that schematically illustrates a method for assessing intracardiac ablation, in accordance with an embodiment of the invention.

FIG. 4 is a flow chart that schematically illustrates a method for assessing intracardiac ablation that is applied at step 72, in accordance with an embodiment of the invention. Processor 40 applies decision logic 80 (typically in software) based on the date collected during ablation (step 64) at a given site, and possibly the data collected before and/or after the ablation (steps 68,70). The following filters may be applied:

A position stability filter 82: Processor 40 measures changes in the location of catheter 24 during the ablation, after compensating for respiratory movement (step 70). Filter 82 typically requires that the variation of the location over a predefined minimum ablation time be no greater than a predefined maximum distance. The variation may be measured, for example, in terms of a standard deviation about the mean position during the ablation time.

A velocity filter 84. This filter can be used to detect loss of stability. For this purpose, processor measures the displacement between successive locations of the catheter and (implicitly or explicitly) divides by the time increment between the locations to find the velocity of motion of the catheter. If the velocity is above a specified threshold, such as 10 mm/sec, the catheter may be considered to be unstable.

An impedance drop filter 86. Processor 40 typically takes the impedance value of the first position in a stable site as a base impedance value, and then tests subsequent impedance values against a predefined percentage threshold. For example, the impedance drop in subsequent measurements may be defined as: (1−current position impedance valuebase impedance value*100. If this drop is greater than the percentage threshold, the site is considered to have been ablated and is therefore marked on map 46. Alternatively or additionally, the amount of impedance drop may be taken into account in coloring the corresponding mark 50, 52.

An ECG drop filter 88. For each stable site, processor 40 may calculate, for example, the maximum peak-to-peak ECG amplitude value in an ECG data span of two seconds ending at the time at which a corresponding position measurement was made. If the calculated amplitude is less than a predefined threshold, the site may be marked as having been ablated and/or colored to indicate the amount of ECG drop.

A force level filter 90. At each stable site, processor 40 tests the average contact force between catheter 24 and the heart tissue against a predefined threshold. When the average contact force is above a predefined threshold, the site is marked as having been ablated and may be colored to indicate the average force level. Additionally or alternatively, processor 40 may assess the force percentage, i.e., the fraction of the time during which the catheter dwelled at a given ablation site for which the force was above a certain force threshold:

$$\left(\frac{\text{number of positions exceeding the contact force threshold}}{\text{total number of positions in the stable site}}\right) * 100.$$

If the percentage value is above a predefined time percentage threshold, the site is marked, and/or the mark may be colored according to the percentage value.

Additionally or alternatively, processor 40 may apply other filters not shown in FIG. 4. For example, if catheter 24 contains a temperature sensor in its distal end, the processor may calculate the temperature increase at each ablation site during the procedure. If the temperature increase is above a predefined threshold, the processor may place a mark at the site. Additionally or alternatively, the mark may be colored according to the temperature increase.

Other collected data and filters may apply to the cumulative amount of RF energy delivered to each site, as well as ultrasound reflectance data if available. Processor 40 may also compute and filter integral measures of the contact force of the catheter against the tissue, which are indicative of the delivery of energy to the tissue. Integral measures of this sort may include, for example, the integral of force over time at a stable location, or the integral of the product of force and RF power.

FIG. 5 is a schematic representation of a part of map 44, showing a series of catheter location data points 100. This figure illustrates how processor identifies and filters ablation sites 102, 104, 106 based on catheter location stability, in accordance with an embodiment of the invention.

Each data point 100 in FIG. 5 indicates a catheter location measurement (after compensation for respiratory movement). The data are collected at predefined time intervals, so that points 100 represent a time sequence of successive catheter locations. A radius 108 defines the spread of catheter locations that can be considered to belong to a single site. Even when operator 22 holds the catheter stably in place against the heart wall, the actual measured position may appear to change due to minor slippage, noise, and imperfect compensation for respiratory motion, for example. Thus, despite the spread of the "clouds" of data points corresponding to sites 102, 104, 106 in FIG. 5, processor 40 considers the data points within each sphere to correspond to the catheter dwelling stably at each of the sites during the respective periods during which the data were collected.

A predefined time threshold determines the length of time that the catheter must dwell at a given site (or equivalently, the number of data points 100 within a given sphere of radius 108) in order for the catheter to be considered to have dwelled stably at the site. Thus, when the number of successive data points 100 within radius 108 around a given center point exceeds the threshold, and RF generator 36 is simultaneously activated, processor 40 may consider the site to have been ablated and may mark the site accordingly. Both radius 108 and the threshold dwell time may be set by operator 22. Processor 40 may decide whether and how to mark a given site based not only on the dwell time, however, but also on other parameters, as explained above.

FIG. 6 shows a schematic plot 110 of catheter contact force at an ablation site, in accordance with an embodiment of the invention. The upper trace in the figure illustrates how processor 40 identifies that catheter 24 is dwelling stably at a given site. Location data are accumulated before and during ablation, at steps 68 and 64 (FIG. 3). The processor accumulates and processes the data over time until it determines, at a time 112, that the location data points over an interval that is equal to a time threshold 114 have all fallen within radius 108. The processor then retrospectively marks a time 116 and the corresponding location as the first stable location at the current ablation site. It is assumed in this example that the catheter remains stable within radius 108 of the current site after time 112, as well.

Concurrently, processor 40 monitors the contact force between catheter 24 and heart 26 to generate and store force plot 110 and computes a running average of the contact force over a time window 120. At a time 118, processor 40 determines that the average force over the time window 120 ending at time 118 has exceeded the contact force threshold that is shown in FIG. 6. (Both the duration of window 120 and the level of the contact force threshold may be set by operator 22.) Processor 40 then marks a time 122 at the beginning of window 120 and the corresponding location of the catheter as the first stable location at the current ablation site at which the catheter exerted sufficient force to ablate the heart tissue at the site.

Beginning from time 122, processor 40 accumulates ablation data over a time interval 124 during which the catheter location stability and average force level continue to satisfy the threshold criteria described above. A progress bar may be presented on display 42 to show operator 22 the cumulative length of effective ablation time at the current site. As explained earlier, the accumulated data during interval 124 may include ECG, tissue impedance, temperature, and/or RF energy delivery, inter alia. The processor filters these data and then marks map 44 accordingly.

FIG. 7 is a schematic representation of a window 130 that may be presented on display 42, in accordance with an embodiment of the invention. The window contains on-screen user controls 132 that operator 22 can use to set the thresholds to be applied by processor 40 to the ablation data values in choosing which ablation sites to mark on map 44. The data parameters and applicable criteria have all been explained above. For each criterion, a checkbox at the left side of the window allows the operator to indicate whether or not processor 40 is to consider the criterion in filtering ablation sites. A slider to the right of each parameter name enables the operator to set the threshold level, within bounds that are set by system 20. For example, the duration (dwell time) for catheter stability may be set to a value between 0 and 60 sec, while the location stability (corresponding to radius 108) may be set to a value between 0 and 8 mm. As another example, the threshold for average contact force may be set to a value between 0 and 150 grams.

Display preference controls 134 in the lower part of window 130 enable the operator to set other aspects of how map 44 will be displayed.

Although window 130 as shown in FIG. 7 permits only a single value of each threshold to be set, in an alternative embodiment (not shown in the figures), operator 22 may input different threshold values for different parts of the heart. Additionally or alternatively, processor 40 may compute different threshold values to apply based on operator inputs and on physiological parameters, such as local heart wall thickness.

FIG. 8 is a schematic representation of 3D map 44 of a heart chamber showing how ablation marks 50 are applied to the map, in accordance with an embodiment of the present invention. In this example, ablation sites that satisfied the threshold criteria at step 72 are assigned to respective positions 140 in a 3D grid at step 74. Processor 40 projects positions 140 onto the nearest respective locations on the surface of map 44, and places marks 50 at these locations.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for performing a medical procedure, comprising:

bringing a probe into contact with an organ in a body of a patient;

displaying a map of the organ and tracking a location of the probe relative to the map;

applying a therapy via the probe at multiple tissue sites in the organ with which the probe is brought into contact;

assessing a stability of the contact between the probe and the tissue sites while applying the therapy; and automatically marking the map, responsively to the assessed stability, to indicate the tissue sites at which the therapy was applied.

2. The method according to claim 1, wherein automatically marking the map comprises accepting a definition of a stability criterion, and marking the sites at which the assessed stability satisfied the stability criterion.

3. The method according to claim 2, wherein accepting the definition comprises setting different, respective definitions for different regions of the organ.

4. The method according to claim 3, wherein the organ has a wall that contains the tissue sites to which the therapy is applied, and wherein setting the different, respective definitions comprises setting different thresholds responsively to variations of a thickness of the wall among the different regions.

5. The method according to claim 2, wherein the stability criterion specifies a minimum time, and wherein the map is automatically marked to indicate the tissue sites at which the probe was stable for no less than the minimum time.

6. The method according to claim 1, wherein assessing the stability comprises measuring changes in the location of the probe during application of the therapy, while compensating for a movement of the body.

7. The method according to claim 6, wherein the organ is a heart, and wherein compensating for the movement comprises compensating for variations in a position of the heart due to respiration.

8. The method according to claim 1, wherein assessing the stability comprises measuring a force of the contact between the probe and the tissue sites.

9. The method according to claim 1, wherein applying the therapy comprises ablating the tissue sites.

10. The method according to claim 9, wherein automatically marking the map comprises measuring an electrical impedance at the tissue sites using the probe, and marking the tissue sites responsively to a change in the impedance during the therapy.

11. The method according to claim 9, wherein automatically marking the map comprises measuring electrophysiological signals at the tissue sites using the probe, and marking the tissue sites responsively to a change in the electrophysiological signals during the therapy.

12. The method according to claim 9, wherein automatically marking the map comprises measuring a temperature at the tissue sites using the probe, and marking the tissue sites responsively to a change in the temperature during the therapy.

13. The method according to claim 9, wherein automatically marking the map comprises measuring electrical power delivered to the tissue sites by the probe, and marking the tissue sites responsively to a cumulative power applied to each of the tissue sites during the therapy.

14. Apparatus for performing a medical procedure, comprising:
an invasive probe, which is configured to be brought into contact with an organ in a body of a patient and to apply a therapy at multiple tissue sites in the organ with which the probe is brought into contact; and
a processor, which is coupled to the probe and is configured to display a map of the organ and to track a location of the probe relative to the map, to assess a stability of the contact between the probe and the tissue sites while applying the therapy, and to automatically mark the map, responsively to the assessed stability, to indicate the tissue sites at which the therapy was applied.

15. The apparatus according to claim 14, wherein the processor is configured to accept a definition of a stability criterion, and to mark the sites at which the assessed stability satisfied the stability criterion.

16. The apparatus according to claim 15, wherein the stability criterion specifies a minimum time, and wherein the processor is configured to automatically mark the map to indicate the tissue sites at which the probe was stable for no less than the minimum time.

17. The apparatus according to claim 15, wherein the processor is configured to accept different, respective definitions of the stability criterion for different regions of the organ.

18. The apparatus according to claim 17, wherein the organ has a wall that contains the tissue sites to which the therapy is applied, and wherein the different, respective definitions comprise different thresholds that are set responsively to variations of a thickness of the wall among the different regions.

19. The apparatus according to claim 14, wherein the processor is configured to assess the stability by measuring changes in the location of the probe during application of the therapy, while compensating for a movement of the body.

20. The apparatus according to claim 19, wherein the organ is a heart, and wherein compensating for the movement comprises compensating for variations in a position of the heart due to respiration.

21. The apparatus according to claim 14, wherein the processor is configured to assess the stability by measuring a force of the contact between the probe and the tissue sites.

22. The apparatus according to claim 14, wherein the therapy applied by the probe comprises ablating the tissue sites.

23. The apparatus according to claim 22, wherein the processor is configured to measure an electrical impedance at the tissue sites using the probe, and to mark the tissue sites on the map responsively to a change in the impedance during the therapy.

24. The apparatus according to claim 22, wherein the processor is configured to measure electrophysiological signals at the tissue sites using the probe, and to mark the tissue sites on the map responsively to a change in the electrophysiological signals during the therapy.

25. The apparatus according to claim 22, wherein the processor is configured to measure a temperature at the tissue sites using the probe, and to mark the tissue sites on the map responsively to a change in the temperature during the therapy.

26. The apparatus according to claim 22, wherein the processor is configured to measure electrical power delivered to the tissue sites by the probe, and to mark the tissue sites on the map responsively to a cumulative power applied to each of the tissue sites during the therapy.

27. A computer software product, comprising a computer-readable medium in which program instructions are stored, which instructions are configured to be read by a processor that is coupled to an invasive probe for applying a therapy at multiple tissue sites in an organ with which the probe is brought into contact, and cause the processor to display a map of the organ and to track a location of the probe relative to the map, to assess a stability of the contact between the probe and the tissue sites while applying the therapy, and to automatically mark the map, responsively to the assessed stability, to indicate the tissue sites at which the therapy was applied.

* * * * *